US010438805B2

(12) United States Patent
Shinagawa

(10) Patent No.: US 10,438,805 B2
(45) Date of Patent: Oct. 8, 2019

(54) METHODS AND SYSTEMS FOR CHAMBER MATCHING AND MONITORING

(71) Applicant: Tokyo Electron Limited, Minato-ku (JP)

(72) Inventor: Jun Shinagawa, San Jose, CA (US)

(73) Assignee: Tokyo Electron Limited, Minato-ku (JP)

( * ) Notice: Subject to any disclaimer, the term of this patent is extended or adjusted under 35 U.S.C. 154(b) by 0 days.

(21) Appl. No.: 15/832,257

(22) Filed: Dec. 5, 2017

(65) Prior Publication Data

US 2018/0158657 A1   Jun. 7, 2018

Related U.S. Application Data

(60) Provisional application No. 62/430,908, filed on Dec. 6, 2016, provisional application No. 62/532,779, filed on Jul. 14, 2017.

(51) Int. Cl.
*H01L 21/3065* (2006.01)
*H01J 37/32* (2006.01)
(Continued)

(52) U.S. Cl.
CPC ......... *H01L 21/3065* (2013.01); *G01N 21/73* (2013.01); *H01J 37/3299* (2013.01);
(Continued)

(58) Field of Classification Search
None
See application file for complete search history.

(56) References Cited

U.S. PATENT DOCUMENTS 7,540,257 B2   6/2009   Kishimoto et al.
7,695,987 B2   4/2010   Davis et al.
(Continued)

OTHER PUBLICATIONS

V. M. Donnelly, "A simple optical emission method for measuring percent dissociations of feed gases in plasmas: Application to $Cl_2$ in a high-density helical resonator plasma", Journal of Vacuum Science and Technology A, JVSTA, vol. 14, No. 3, May/Jun. 1996, pp. 1076-1087.

(Continued)

*Primary Examiner* — Jiong-Ping Lu
(74) *Attorney, Agent, or Firm* — Oblon, McClelland, Maier & Neustadt, L.L.P.

(57) ABSTRACT

A method and a system for plasma etching are provided. The method includes measuring a first set of plasma etch processing parameters; determining an etch rate; altering the plasma etch processing chamber hardware configuration if the determined etch rate differs from a standard etch rate by more than a predetermined etch rate difference threshold, thereafter repeating the determining and altering until the determined etch rate differs from the standard etch rate by less than the predetermined etch rate difference threshold. The method further includes measuring a critical dimension of an etched feature and altering the etch processing parameters if the measured critical dimension differs from a standard critical dimension by more than a predetermined critical dimension difference threshold, thereafter repeating the determining and altering until the measured critical dimension differs from the standard critical dimension by less than the predetermined critical dimension difference threshold.

18 Claims, 11 Drawing Sheets

(51) Int. Cl.
*H01L 21/66* (2006.01)
*G01N 21/73* (2006.01)
*H01L 21/67* (2006.01)
*G01J 3/443* (2006.01)
*G01N 21/68* (2006.01)

(52) U.S. Cl.
CPC .. *H01J 37/32183* (2013.01); *H01J 37/32935* (2013.01); *H01J 37/32972* (2013.01); *H01J 37/32981* (2013.01); *H01L 22/10* (2013.01); *H01L 22/12* (2013.01); *H01L 22/20* (2013.01); *G01J 3/443* (2013.01); *G01N 21/68* (2013.01); *H01J 2237/24507* (2013.01); *H01J 2237/24585* (2013.01); *H01J 2237/334* (2013.01); *H01L 21/67069* (2013.01); *H01L 21/67248* (2013.01); *H01L 21/67253* (2013.01); *H01L 22/26* (2013.01)

(56) References Cited

U.S. PATENT DOCUMENTS

| | | |
|---|---|---|
| 8,368,308 B2 | 2/2013 | Banna et al. |
| 9,082,594 B2 | 7/2015 | Valcore, Jr. et al. |
| 9,378,930 B2 | 6/2016 | Grimbergen et al. |
| 2005/0199341 A1* | 9/2005 | Delp ............... H01J 37/32 156/345.24 |

OTHER PUBLICATIONS

Kye Hyun Baek, et al., "Implementation of a robust virtual metrology for plasma etching through effective variable selection and recursive update technology", Journal of Vacuum Science & Technology B, JVSTB, vol. 32. No. 1, Jan./Feb. 2014, pp. 012203-1-012203-10.

Jane P. Chang, et al., "Kinetic study of lo energy argon ion-enhanced plasma etching of polysilicon with atomic/molecular chlorine", Journal of Vacuum Science and Technology A, vol. 15, No. 4, Jul./Aug. 1997, pp. 1853-1863.

C. C. Hsu, et al., "Measurement and modeling of time- and spatial-resolved water surface temperature in inductively coupled plasmas", Journal of Vacuum Science and Technology A, JVSTA, May/Jun. 2007, vol. 25, No. 3, pp. 607-614.

Richard A. Gottscho, et al., "Microscopic uniformity in plasma etching" Journal of Vacuum Science & Technology B, vol. 10, No. 5, Sep./Oct. 1992, pp. 2133-2147.

Nobuyuki Kuboi, et al., "Effect of open area ratio and pattern structure on fluctuations in critical dimension and Si recess[a])", Journal of Vacuum Science and Technology A, vol. 31, No. 6, Nov./Dec. 2013, pp. 061304-1-061304-9.

* cited by examiner

METHODS AND SYSTEMS FOR CHAMBER MATCHING AND MONITORING

CROSS-REFERENCE TO RELATED APPLICATIONS

This application claims the benefit of priority from U.S. Provisional Application No. 62/430,908 filed Dec. 6, 2016 and U.S. Provisional Application No. 62/532,779 filed Jul. 14, 2017, both of which are incorporated herein by reference in their entirety.

BACKGROUND OF THE INVENTION

Chamber matching is a condition where the output of multiple plasma processing chambers, in terms of properties of devices produced, are exactly matched within the specification.

In a manufacturing environment, a process recipe is typically tuned to match metrology values such as critical dimension (CD) and etch rate (ER). This approach, however, requires at least taking processed substrates from the process line, for testing and metrology, resulting in lost productivity. Furthermore, some metrology techniques are destructive, by nature, resulting in lost revenue due to substrates being destroyed to verify etch rate (ER), and even more importantly, critical dimension (CD). The need exists for a diagnostic that would allow chamber matching and process tuning to be ascertained without the time-consuming routing of processed substrates to metrology stations, or the even more costly destructive metrology techniques. Such novel diagnostics would leverage data collected from existing sensors on the plasma processing chamber, to ensure chamber matching and in-spec critical dimension (CD) and etch rate (ER).

In prior art chamber matching, matching module-level sensor values, such as, for example, matching capacitance positions on the match network, do not guarantee matching of the plasma parameters during device production, and hence produced device characteristics. Sensor to sensor variations typically make direct matching of sensor values not useful. Furthermore, the use of statistical fault detection systems requires a user-defined boundary to be defined between normal and abnormal states, for example between normal and abnormal plasma states, as defined by CD metrology data obtained from processed devices. Since there do not exist direct links between, the parameters (controlled and measured), and critical dimension (CD), there is a tendency for such systems to over-diagnose faults. In other words, an increase of the frequency of fault detections may occur when, in-fact, the produced devices are still within-specification. For example, some benign parameter excursion can trigger a false fault detection. Or, in terms of application in chamber matching, post-maintenance seasoning, etc., a slight mismatch of some parameter which is not detrimental to produced device characteristics may cause maintenance personnel to not return the chamber into production for an extended period of time, resulting in unnecessary revenue loss. To address the above shortcomings, the invention described herein establishes a more reliable boundary between normal conditions, and faulty or mismatched chamber state, based on a more direct linkage between plasma parameters and critical dimension (CD).

Accordingly, what is needed, as recognized by the present inventor, is a method and a system capable of minimizing device performance mismatch by matching plasma conditions across multiple chambers.

The foregoing "Background" description is for the purpose of generally presenting the context of the disclosure. Work of the inventor, to the extent it is described in this background section, as well as aspects of the description which may not otherwise qualify as prior art at the time of filing, are neither expressly or impliedly admitted as prior art against the present invention.

SUMMARY OF THE INVENTION

An aspect of the present disclosure includes a method for plasma etching. The method includes measuring a first set of plasma etch processing parameters; determining an etch rate; altering the plasma etch processing chamber hardware configuration if the determined etch rate differs from a standard etch rate by more than a predetermined etch rate difference threshold, thereafter repeating the deters fining and altering until the determined etch rate differs from the standard etch rate by less than the predetermined etch rate difference threshold. The method further includes measuring a critical dimension of an etched feature and altering the etch processing parameters if the measured critical dimension differs from a standard critical dimension by more than a predetermined critical dimension difference threshold, thereafter repeating the determining and altering until the measured critical dimension differs from the standard critical dimension by less than the predetermined critical dimension difference threshold.

Another aspect of the present disclosure includes a method. The method includes monitoring in-situ changes for at least one plasma parameter of a plasma in a vacuum process chamber and at least one process condition in the vacuum process chamber; the process condition being a temperature, a gas flow, a power level, a power frequency level, the plasma parameter being a density of the a constituent of the plasma, determining magnitudes of the in-situ changes for the plasma parameter(s) and the process parameter(s); determining the magnitude changes relative to each other for at least two of the plasma parameter(s), process parameter(s), or a combination thereof; and adjusting at least one of the process conditions of the vacuum process chamber based, at least in part, at least one magnitude comparison between the plasma parameter(s), the process parameter(s), or a combination thereof.

Another aspect of the present disclosure includes a plasma etching system. The system includes a plasma, etch processing chamber and a controller. The controller is configured to acquire a first set of plasma etch processing parameters; determine an etch rate from the measured first set of plasma etch processing parameters; alter the plasma etch processing chamber hardware configuration if the determined etch rate differs from a standard etch rate corresponding to the standard set of etch processing parameters by more than a predetermined etch rate difference threshold, thereafter repeating the steps of acquiring, determining, and altering until the determined etch rate differs from the standard etch rate by less than the predetermined etch rate difference threshold. The controller is further configured to measure a critical dimension of an etched feature formed on a substrate; and alter the etch processing parameters for the plasma etch processing if the measured critical dimension differs from a standard critical dimension corresponding to the standard set of etch processing parameters by more than a predetermined critical dimension difference threshold, thereafter repeating steps of measuring and altering until the measured critical dimension differs from the standard critical dimension by less than the predetermined critical dimension difference threshold.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings wherein.

DETAILED DESCRIPTION

Figure 1:
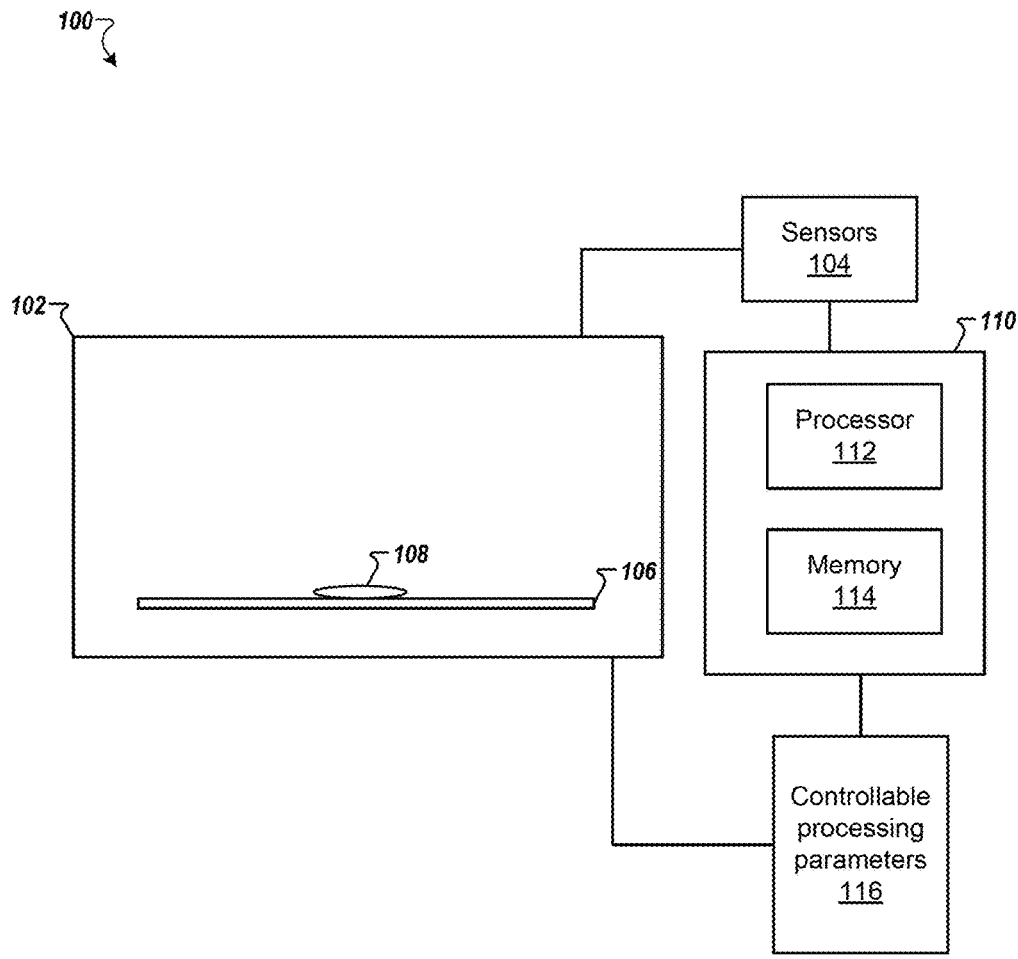
FIG. 1 is a side view schematic of a plasma processing system according to one example.

Referring now to the drawings, wherein like reference numerals designate identical or corresponding parts throughout several views, the following description relates to systems and associated methodologies for monitoring, diagnosing, and matching processing chambers.

Reference throughout the specification to "one embodiment" or "an embodiment" means that a particular feature, structure, material, or characteristic described in connection with the embodiment is included in at least one embodiment, but do not denote that they are present in every embodiment. Thus, the appearances of the phrases "in one embodiment" in various places through the specification are not necessarily referring to the same embodiment. Furthermore, the particular features, structures, materials, or characteristics may be combined in any suitable manner in one or more embodiments.

An etching system or tool may include multiple chambers (e.g., five chambers). The multiple chambers in the etching system or in a mass production environment (e.g., fabrication plant) are matched to produce devices having matched electrical performance with a predetermined specification. A critical dimension (CD) and an etching rate (ER) are matched across the multiple chambers. During preventive maintenance the chamber may be cleaned and one or more parts may be replaced which may alter the critical dimension (CD) and the etching rate (ER). The etching rate (ER) and the critical dimension (CD) of the chamber have to be checked before putting the chamber in a production line. Chamber matching may also be performed when a chamber is reintroduced into mass production after repairs or being offline for a period of time. Further, during production the critical dimension (CD) and the etch rate (ER) may be monitored to ensure that fabricated devices conform to a target specification.

Critical dimension (CD) is related to the electrical properties of the fabricated electrical components (e.g., transistor), thus, having uniform critical dimension (CD) across devices fabricated using different chambers is critical.

Plasma processing system chamber diagnostics can measure physical parameters, including an ion flux ($\Gamma_{ion}$) and a neutral flux ($\Gamma_n$) which are directly related to the vertical and horizontal etch rates via the relationship (see Jane Cheng et al., "Kinetic study of low energy argon", J. Vac. Sci. Technol. A 15(4), July/August 1997 and Richard A Goftscho et al., "Microscopic uniformity in plasma etching", J. Vac. Sci. Technol. B 10(5), September/October 1992):

$$ER \sim a\Gamma_n/(b\Gamma_n/\Gamma_{ion}+1) \leftrightarrow CD=ER_{Horizontal} \qquad (1)$$

where a and b are constants.

The horizontal etch rate, which can be determined from the vertical etch rate ER, is related to the critical dimension (CD). Therefore, knowing the ion flux and the neutral flux allows a determination of both the etch rate (ER) and the critical dimension (CD), which are the primary determinants of etch process outcome, and therefore can be used to assess process chamber matching and readiness for process.

Diagnostics measurements are independent from variabilities such as sensor to sensor and installation to installation variability. Diagnostics measurements are readily available and more importantly non-invasive with minimal impact on plasma processing chamber, making them ideal for uses in a manufacturing facility.

Measuring the ion flux and the neutral flux in a processing chamber may require complex instruments that may not be easily fitted in the processing chamber. In one implementation, proxies (i.e. proxy parameters) may be used to estimate the ion flux ($\Gamma_{ion}$) and the neutral flux ($\Gamma_r$). For example, a rate of change of temperature dT/dt of a surface exposed to the plasma (e.g., substrate) is related and can be used to measure the ion energy flux and may be used as a proxy for the ion flux (i.e., the ion flux is proportional to dT/dt). The higher the ion energy flux, the higher the temperature rise. The rise in temperature of the surface measurement may be performed in-situ, using a temperature sensor. Actinometry measurement using an optical emission spectrometer (OES) sensor may be used to determine the neutral flux. For example, a pair of predetermined spectral lines may be monitored (e.g., Chlorine and Argon line strengths), and a ratio of the strength is related to the neutral chlorine density and the neutral flux. In other implementations, other sensors that measure one or more variables/parameters proportional to the ion flux ($\Gamma_{ion}$) and the neutral flux ($\Gamma_n$) may be used.

In one implementation a peak to peak voltage ($V_{pp}$) of the substrate (e.g., voltage of an electrical signal applied to the electrode) is used as a proxy for the ion flux as the peak to peak voltage ($V_{pp}$) correlates to the electric field with which ions are accelerated to the substrate surface.

In one implementation, deviations in the proxies may be used to monitor the production process as described further below.

FIG. 1 is a side view schematic of a plasma processing system 100 according to one example. The plasma processing system 100 includes a processing chamber 102 (i.e., a plasma etch processing chamber, a plasma processing chamber, a vacuum process chamber). The plasma processing system 100 is equipped with sensors or probes 104 (e.g., OES) that measure one or more parameters during a plasma etching process in the processing chamber 102. A substrate holder 106 (e.g., an electrostatic chuck, a vacuum chuck) is disposed inside the processing chamber 102 for receiving a substrate 108 (e.g., semiconductor wafer, integrated circuit, a sheet of a polymer material to be coated, a metal to be surface hardened by ion implantation, or other semiconductor material to be etched or deposited). Radio frequency (RF) and/or microwave (MW) power from an radio frequency (RF) and/or microwave (MW) source (not shown) is supplied to the processing chamber 102 to ignite and sustain a plasma proximate to the substrate 108, wherein the energetic chemical species from the plasma are used to perform a plasma processing step on the substrate 108.

In one implementation, the energy source is an antenna powered by a radio frequency (RF) source to inductively couple radio frequency (RF) energy into the processing chamber 102. An electromagnetic field generated by the application of radio frequency (RF) power to the antenna energizes the process gas to form the plasma above the substrate 108.

In one implementation, an electrode may be used to couple radio frequency (RF) energy to plasma.

In one implementation, the processing chamber 102 includes an upper electrode (i.e., top electrode) and a lower electrode (i.e., bottom electrode) (not shown). The upper electrode may be located opposite and facing the substrate holder 106. The upper electrode and the lower electrode may be made of a metal (e.g., aluminum, alloy of aluminum, copper). The top electrode power level comprises a microwave (MW) frequency power level. The bottom electrode power level comprises a radio frequency (RF) power level.

Processing gases are flown into the plasma processing chamber 102 (not shown) and a pumping system is provided (not shown) to maintain a vacuum in the plasma processing chamber 102, at a desired process pressure. Examples of plasma processing steps include plasma etching, plasma-enhanced chemical vapor deposition (PECVD), plasma-enhanced atomic layer deposition (PEALD), and the like.

A controller 110 controls a gas, supply valve (not shown) to facilitates supply of a gas from a gas reservoir to gas inlets of the processing chamber 102 to control pressure within the processing chamber 102.

Processing parameters for the plasma etch processing chamber are set to a predetermined standard set of etch processing parameters by the controller 110. Then, the plasma is ignited in the processing chamber 102.

The controller 110 may include a processor 112 and a memory 114. The processor 110 may be a general purpose computer as shown and described in FIG. 10. The controller 110 may also control controllable processing parameters 116.

The memory 114 may store variables related to a preferred ion flux of a plasma (e.g., ion flux) generated in a "golden" (a standard or reference) process chamber, and one or more variables related to preferred neutral flux of the plasma (e.g., neutral flux). The one or more variables related to the preferred ion flux may include a temperature change of the substrate over a period of time, while the substrate is exposed to the matching plasma. The one or more variables related to the preferred radical flux may include a density of at least one constituent of the matching plasma. The constituent may include a neutrals etchant such as a halogen constituent (e.g., chlorine, bromine, or fluorine), oxygen, hydrogen, or nitrogen. The memory 114 may also store adjustments to the processing chamber 102. As described in more details below, the adjustments may include changes to power levels and/or to the flow rates of gases to the processing chamber 102.

In one implementation, the processor 112 may receive process chamber characteristics from the processing chamber 102 that includes one or more variables related to the actual ion flux and one or more variables related to the actual neutral flux of the processing chamber 102. The processor 112 may determine a difference between the preferred chamber characteristics and the process chamber characteristics. The processor 112 may determine adjustments based on the difference. Further, the processor 112 may send a signal to the processing chamber 102 to adjust one or more parameters (e.g., controllable processing parameters 116) based on the determined adjustments.

In one implementation, the processor 112 may generate a model for the critical dimension (CD) based on one or more plasma parameters.

In one implementation, the methodologies described herein may be implemented during preventive maintenance on a processing chamber. When the processing chamber goes through preventive maintenance the etch rate (ER) and the critical dimension (CD) may change and may not match the previous etch rate (ER) and critical dimension (CD) of the chamber (i.e., before maintenance).

Figure 2:
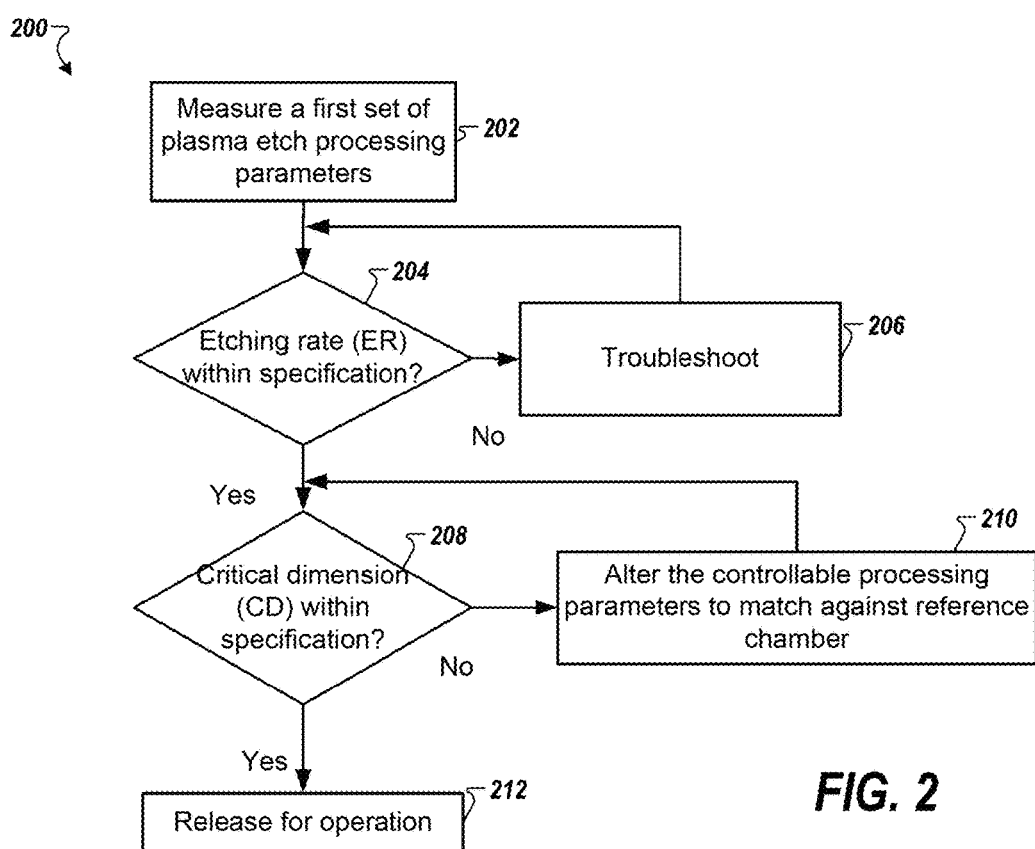
FIG. 2 is a flowchart that shows a method for performance matching by absolute plasma diagnostics according to one example.

FIG. 2 is a flowchart that shows a method 200 for performance matching by absolute plasma diagnostics according to one example. At step 202, a first set of plasma etch processing parameters is measured. For example, the first set of plasma etch processing parameters may include an ion flux ($\Gamma_{ion}$) and a neutral flux ($\Gamma_n$). In another implementation, the first set of plasma etch processing parameters may include one or more proxies for the ion flux and the neutral flux.

At step 204, an etch rate from the first set of plasma etch processing parameters is determined by the processor 112. Then, the processor 112 check to see whether the etch rate differs from a standard etch rate that corresponds to a standard set of etch processing parameters by more than a predetermined etch rate difference threshold (e.g., 5%, but may vary from 0.5% to 10%, depending on the ultimate device performance tolerances). In response to determining that the etch rate differs from the standard etch rate by more than the predetermined etch rate difference threshold, the process proceeds to step 206. In response to determining that the etch rate differs from the standard etch rate by less than the predetermined etch rate difference threshold, the process proceeds to step 208.

At step 206, the processing chamber hardware configuration is altered (e.g., check for loose screws, loose parts, eroded or consumed parts, and other hardware faults). The process is repeated until the etch rate differs from the standard etch rate by less than the predetermined etch rate difference threshold.

At step 208, a critical dimension (CD) of an etched feature formed on the substrate is determined. Then, the processor 112 check to see whether the critical dimension (CD) differs from a standard critical dimension (CD) that corresponds to the standard set of etch processing parameters by more than a predetermined critical dimension (CD) difference threshold. In response to determining that the critical dimension (CD) differs from the standard critical dimension (CD) by more than the predetermined critical dimension (CD) difference threshold, the process proceeds to step 210. In response to determining that the critical dimension (CD) differs from the standard critical dimension (CD) by less than the predetermined critical dimension (CD) difference threshold, the process proceeds to step 212.

At step 210, the plasma etch processing parameters for the plasma etch processing are altered (e.g., tweak in flow rate, temperature). For example, controllable processing parameters may be altered to match against a reference chamber as described later herein.

At step 212, the processing chamber is released for operation. Production substrates using the altered plasma etch processing chamber hardware configuration and the altered etch processing parameters may be etched.

In one implementation, the critical dimension of the etched feature may be measured using a nondestructive optical measurement method (e.g., optical critical dimension (OCD) measurement method), or other method such as scanning electron microscopy (which may be destructive, or not, depending on type).

In one implementation, the critical dimension (CD) may be determined from the set of plasma etch processing parameters.

In one implementation, the critical dimension (CD) may be a function of the etching rate (ER) and a by-product layer or a pre-cursor layer. The by-product layer or the pre-cursor layer may be measured by an optical emission spectrometer (OES). The by-product layer is a passivation layer formed by deposition of the etch by-product (e.g., SiCl). The pre-cursor is a passivation layer formed by the pre-cursor deposition molecule which is mixed in input gas.

Figure 3:
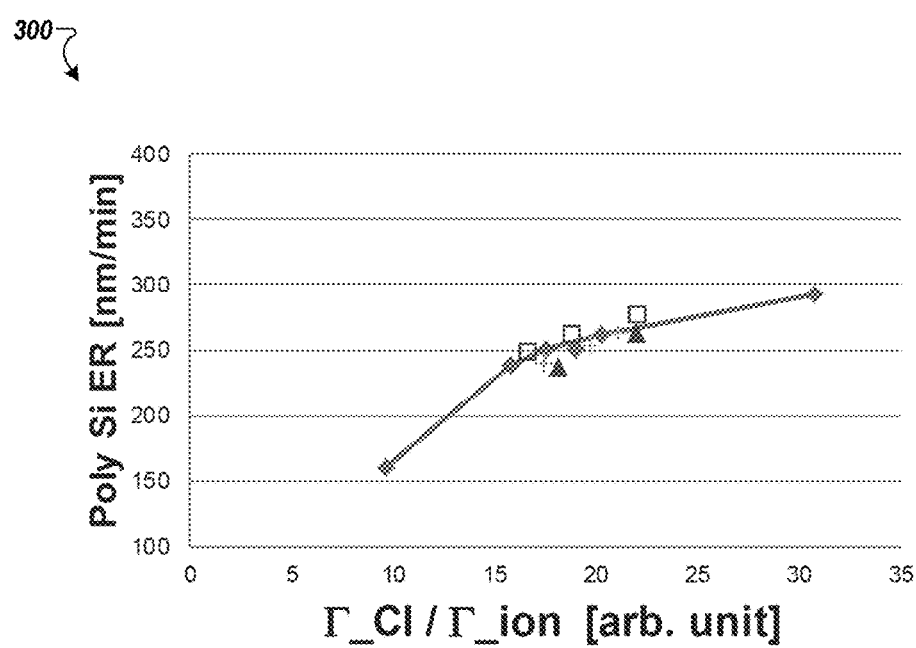
FIG. 3 is a schematic that shows etching rates according to one example.

FIG. 3 is a schematic 300 that shows the etching rate (ER) according to one example. Schematic 300 shows the etch rate (ER) as a function of the chlorine flux and the ion flux.

As described previously, the methods described herein may be implemented during production, preventive maintenance, calibrations, seasoning, and post preventive maintenance chamber matching. The seasoning can be terminated when the chamber is stabilized where stability is monitored by the ion flux ($\Gamma_{ion}$) and the neutral flux ($\Gamma_n$) This has the advantage over current implementations of running a fixed number of wafers to stabilize a chamber, which may lead to wasting substrates, chemicals, and unnecessarily long processing chamber downtime. The preventive maintenance monitor terminates the wafer run when the critical dimension (CD) drifts exceeds a predetermined threshold with the critical dimension (CD) estimated based on $\Gamma_{ion}$ and $\Gamma_n$.

Figure 4:
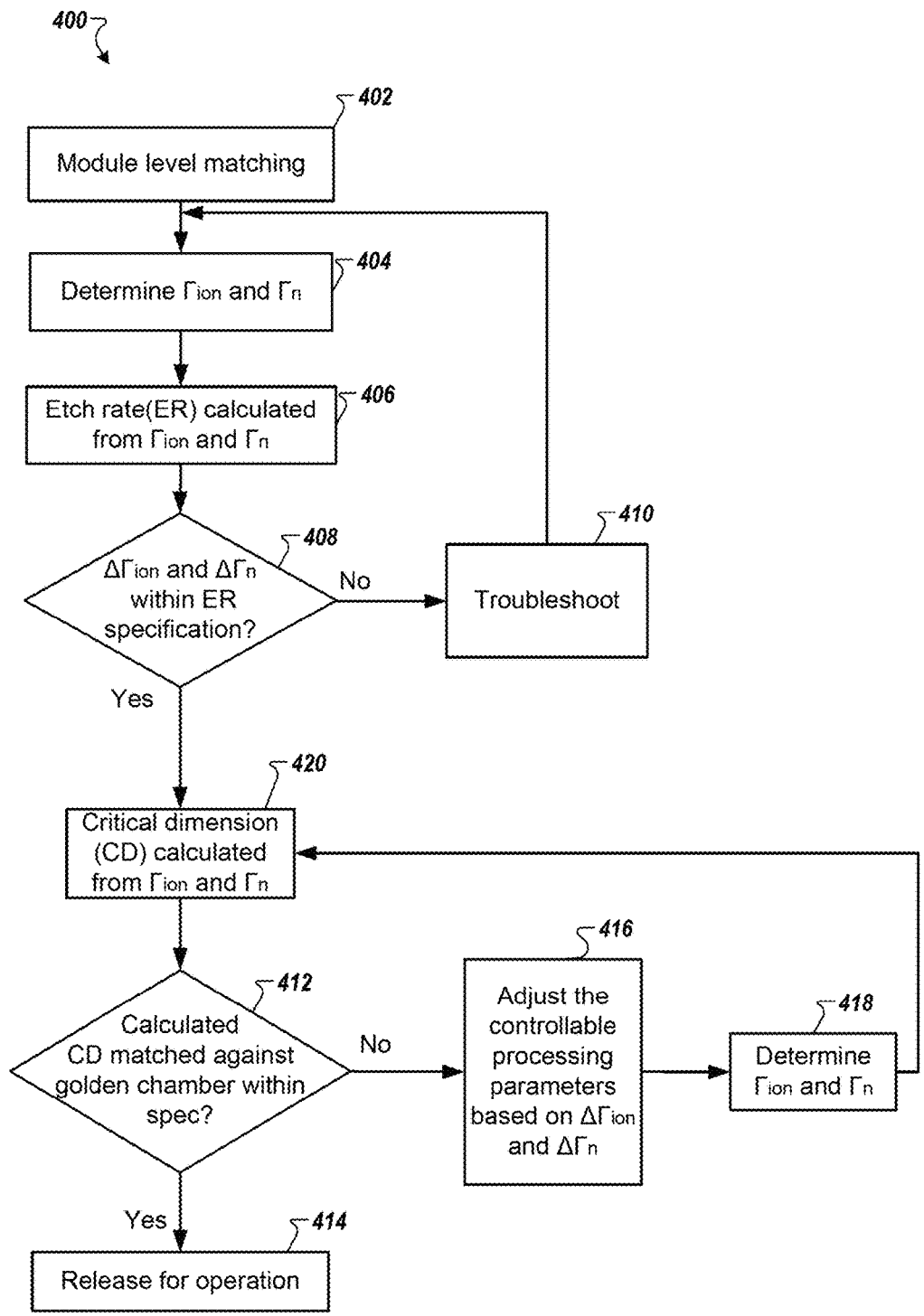
FIG. 4 is a flowchart that shows a method for matching the processing chamber based on plasma diagnostics according to one example.

FIG. 4 is a flow chat that shows a method 400 for device performance matching according to one example. At step 402, a matching process may be initialized.

At step 404, the ion flux ($\Gamma_{ion}$) and the neutral flux ($\Gamma_n$) may be determined. At step 406 the etch rate (ER) may be determined from the ion flux and the neutral flux.

At 408, the controller 110 may check to see whether the deviation in the ion flux ($\Gamma_{ion}$) and the neutral flux ($\Gamma_n$) is within the specification. In response to determining that the deviation in the ion flux ($\Gamma_{ion}$) and the neutral flux ($\Gamma_n$) is within a tolerable threshold, the process proceeds to step 412. In response to determining that the deviation is not within the predetermined tolerable threshold the process proceeds to step 410. At step 410, hardware troubleshooting is performed.

At step 412, the processor 112 may determine the critical dimension (CD). The processor 112 may check to see whether the critical dimension (CD) matched against the "golden" chamber is within the predetermined specification. In response to determining that the critical dimension (CD) is within specification, the chamber is released for operation at step 414. In response to determining that the critical dimension (CD) matched against the "golden" chamber are not within specification, the process proceeds to step 416. At step 416, the controllable processing parameters may be altered by the processor 112 to match the critical dimension (CD). Then, the process proceeds to step 418.

The etch processing parameters may be altered based on a difference between the $\Gamma_{ion}$ and $\Gamma_n$ and a standard ion flux ($\Gamma_{ion\ std}$) and a standard neutral flux ($\Gamma_{n\ std}$) corresponding to the standard set of etch processing parameters. For example, the ion flux ($\Gamma_{ion}$) may be compared to the standard ion flux ($\Gamma_{ion\ std}$) and the neutral flux ($\Gamma_n$) may be compared to the standard neutral flux ($\Gamma_{n\ std}$). The etch processing parameters may be altered if either flux differs from the standard flux by more than a predetermined difference threshold.

The power level applied to the lower electrode disposed in the processing chamber may be changed. In one example, $\Delta\Gamma_{ion}=\Delta P_{RF}$ as described later herein. The power lever applied to the top electrode may also be changed. The gas flow rate of a gas flowing into the processing chamber may also be changed.

At step 418, the ion flux ($\Gamma_{ion}$) and the neutral flux ($\Gamma_n$) may be determined. At step 420, the critical dimension (CD) is determined based on the ion flux and the neutral flux. Then, the process proceeds to step 412.

In one implementation, a number density of chlorine neutrals (n_Cl), determined using optical emission spectroscopy (OES), may be used as a proxy for the neutral flux (i.e., in a chlorine plasma for e.g. polysilicon etch).

Figure 5A:
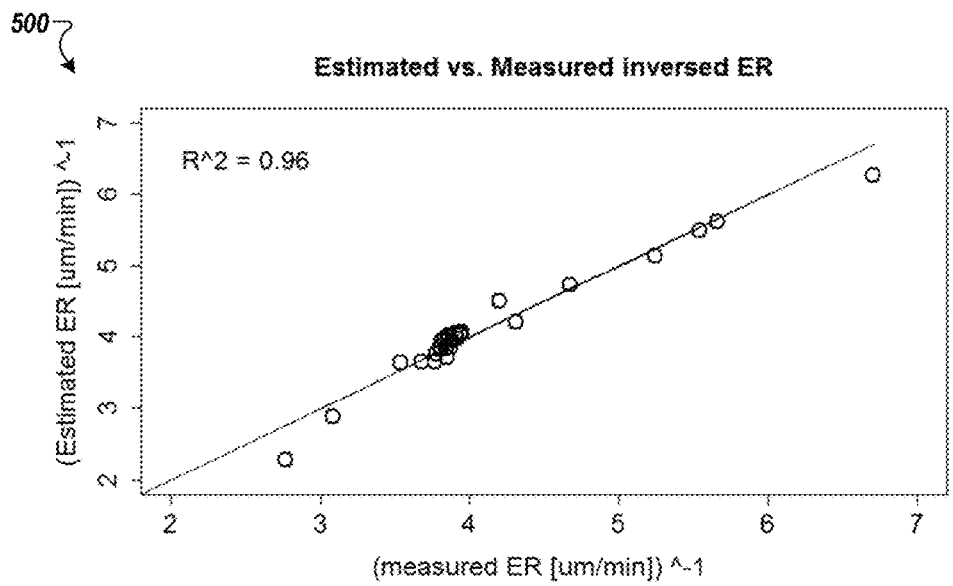
FIGS. 5A-5D are schematics that show the etching rate versus a plurality of parameters according to one example.

FIG. 5A is a schematic 500 that shows the estimated etching rate versus the measured etching rate. The estimated etching rate is based on a first proxy $\Gamma_{ion1}$, a second proxy ($\Gamma_{ion2}$), and a third proxy ($n_{neutral}$). In one implementation, the first proxy may correspond to dT/dt, the second proxy may correspond to Vpp, and the third proxy to n_Cl.

Figure 5B:
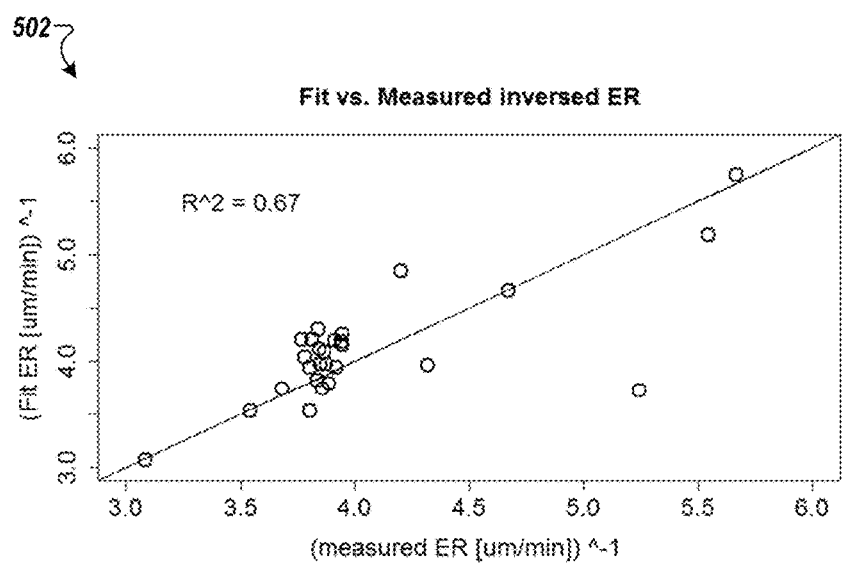
Figure 5C:
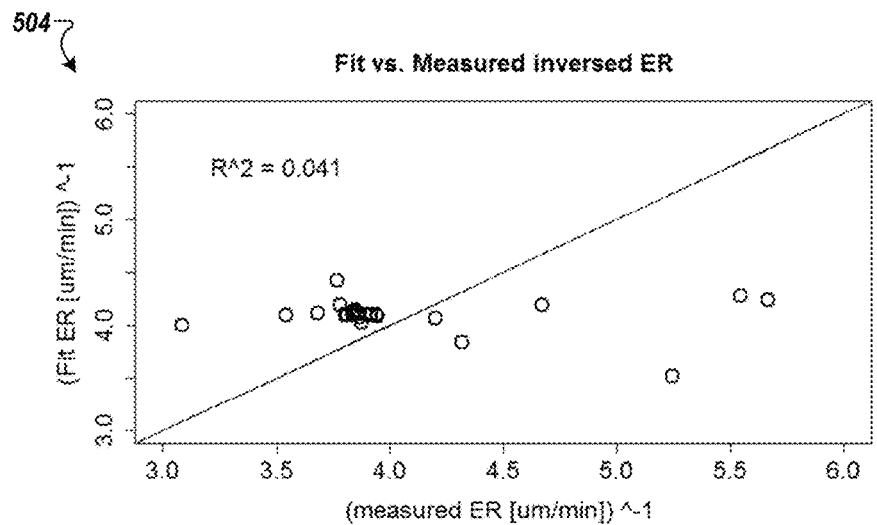
Figure 5D:
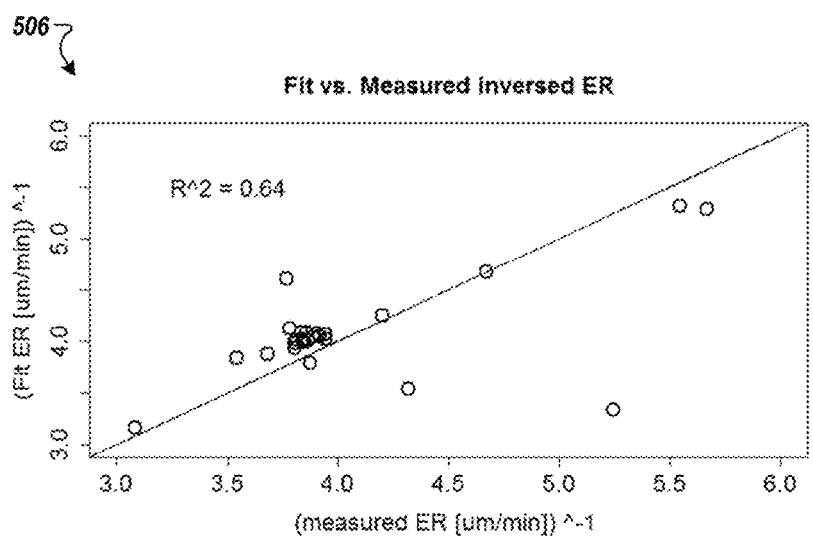

The estimated ER as a function of the first proxy (i.e., ER~f(dT/dt) is shown in schematic 502 of FIG. 5B. The estimated ER as a function of the third proxy (i.e., ER~f(nCl) is shown in schematic 504 of FIG. 5C. The estimated ER as a function of the second proxy (i.e., ER~f(Vpp) is shown in schematic 506 of FIG. 5D. The data in FIGS. 5A-D were collected from a single chamber over multiple substrate processing runs. As shown in FIG. 5A-D, the matching of the first proxy, the second proxy, and the third proxy is very robust across many processing runs, and across installations following chamber maintenance and fault repair.

The controllable parameters of the processing chamber (i.e., process parameters) may include a bias power (BP) which is the power applied to the substrate holder, which generates the electric field that attracts the ions out of the plasma, a source power (SP) that is applied to generate a plasma that provides a source of the ions and neutrals, and the flow rate (FR) of chlorine (Cl2). In one implementation, the statistical model for the processing parameters may include:

$$\Delta n_{neutral}=b_1\Delta BP+b_2\Delta SP+b_3\Delta FR$$

$$\Delta\Gamma_{ion1}=c_1\Delta BP+c_2\Delta SP+c_3\Delta FR$$

$$\Delta\Gamma_{ion2}=d_1\Delta BP+d_2\Delta SP+d_3\Delta FR$$

where $b_1$, $b_2$, $b_3$ are fitting parameters for $\Delta n_{neutral}$ associated with $\Delta BP$, $\Delta SP$, and $\Delta FR$ respectively, $c_1$, $c_2$, $c_3$ are fitting parameters for $\Delta\Gamma_{ion1}$ associated with $\Delta BP$, $\Delta SP$, and $\Delta FR$ respectively, and $d_1$ $d_2$, $d_3$ are fitting parameters for $\Delta F_{ion2}$ associated With $\Delta BP$, $\Delta SP$, and $\Delta FR$ respectively.

TABLE 1

Fitting parameters for the process parameters.

|  |  | $\Delta ER$ | $\Delta n_{neutral}$ | $\Delta\Gamma_{ion1}$ | $\Delta\Gamma_{ion2}$ |
|---|---|---|---|---|---|
| $\Delta FR$ | A0 | −3.4 | 5 | −4.4 | 2.1 |
|  | Slope | 0.27 | 1.1 | −0.1 | −0.28 |
|  | R2 | 0.69 | 0.98 | 0.63 | 0.98 |
| $\Delta SP$ | A0 | 1.3 | −1.8 | −4.4 | 0.54 |
|  | Slope | 0.28 | 0.062 | 0.47 | 0.14 |
|  | R2 | 0.98 | 0.5 | 0.9 | 0.94 |
| $\Delta BP$ | A0 | −7 | 12 | −3.9 | −3 |
|  | Slope | 0.82 | −0.59 | 0.84 | 0.66 |
|  | R2 | 0.95 | 0.77 | 1 | 0.99 |

Figure 6:
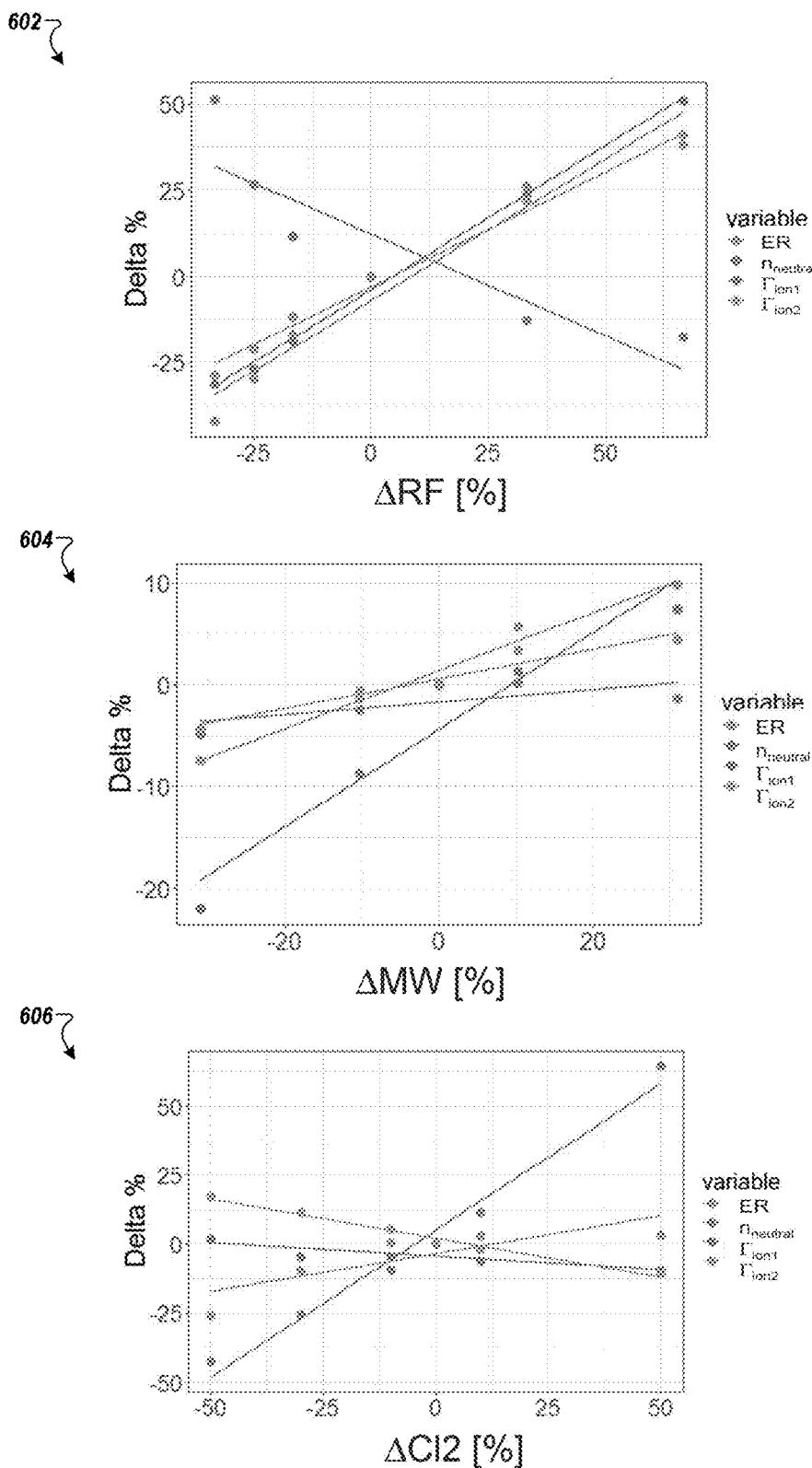
FIG. 6 is a schematic that shows the controllability of the processing parameters according to one example.

FIG. 6 is a schematic that shows the controllability of the processing parameters according to one example (i.e., sensitivity of the plasma parameters to the controllable parameters of the chamber). Graph 602 shows the change in radio frequency (RF) power for changes in the etch rate (ER), a first proxy $\Gamma_{ion1}$, a second proxy $\Gamma_{ion2}$, and a third proxy $n_{neutral}$. Graph 604 shows the change in microwave (MW) power for changes in the etch rate (ER), $\Gamma_{ion1}$, $\Gamma_{ion2}$ and $n_{neutral}$. Graph 606 shows the flow rate of Cl2 for changes in the etch rate (ER), $\Gamma_{ion1}$, $\Gamma_{ion2}$ and $n_{neutral}$.

Figure 7:
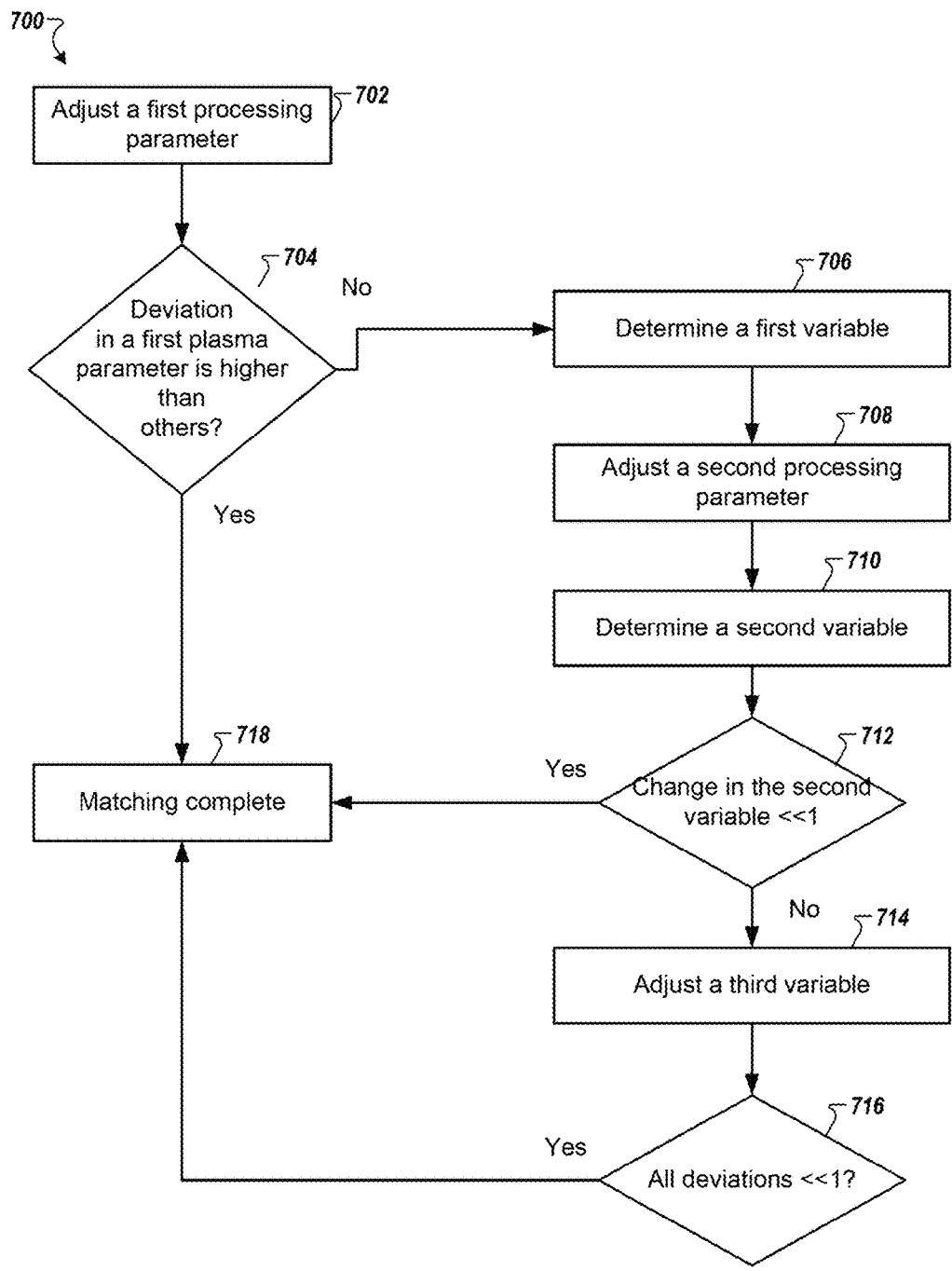
FIG. 7 is a flowchart that shows a chamber matching process according to one example.

FIG. 7 is a flowchart that shows a chamber matching process 700 according to one example. Process 700 may be implemented before or after preventive maintenance. In one implementation, the controllable processing parameters may be adjusted by decreasing sensitivity (i.e., the controllable processing parameters with highest sensitivity are adjusted first). The sensitivities associated with a particular processing chamber 102 may be stored in memory 114 of the controller 110.

At step 702, a first process parameter (i.e., a process condition) may be adjusted. In one implementation, a gas flow rate may be adjusted to achieve a desired result on a substrate. The adjustment of $Cl_2$ may be a function of the difference in the third proxy. For example, $\Delta Cl_2 \sim n_{neutral}/1.1$, where 1.1 is the sensitivity in Table 1. At step 704, the processor 112 may check to see whether the deviation of a first plasma parameter is much larger than the deviation in a second and a third plasma parameters. In response to determining that the deviation of the first plasma parameter is much larger than the deviations in the second and the third plasma parameters, then the process proceeds to step 718. In response to determining that the deviation of the first plasma parameter is not much larger (e.g., 10%) than the deviation in the second and the third plasma parameters, then the process proceeds to step 706. At step 706, the processor 112 may determine a change in the second plasma parameter. For example, $\Delta F_{ion}2 \sim \Gamma_{ion2} - 0.3 \times \Delta Cl_2$. At step 708 a second process parameter may be adjusted. For example, the radio (RF) bias power may be adjusted as: $\Delta\Gamma_{ion}2 \sim \Delta BP/0.66$. At step 710, the processor 112 may determine a second variable based on a deviation in the third plasma parameter. For example, $\Delta\Gamma_{ion1}\_2 \sim \Delta\Gamma_{ion1} + 0.84 \times \Delta BP$. At step 712, the processor 112 may determine whether the second parameter is less than a predetermined threshold value. In response to determining that the deviation of the second variable is less than the predetermined threshold value the process proceeds to step 718. In response to determining that the deviation is not less than the predetermined threshold value, the process proceeds to step 714. At step 714, the knob for a third processing parameter is adjusted (e.g., source power). For example, $\Delta\Gamma_{ion1}\_2 \sim \Delta SP/0.47$. At step 716, the processor 112 may check to see whether the deviations in the first, second, and third plasma parameters are less than the predetermined threshold values. In response to determining that the deviations are less than the predetermined threshold value, the process proceeds to step 718. At step 718, the matching is completed. For example, an indication may be output that the matching is completed. In response to determining that one or more of the deviations in the plasma parameters are not less than the predetermined threshold value, the process proceeds to step 704.

In one implementation, the critical dimension (CD) may be correlated to the plasma parameters, directly. In other implementations, the ion flux ($\Gamma_{ion}$) and the neutral flux ($\Gamma_n$) may be used to bridge the gap between the critical dimension and the plasma parameters (i.e., sensor data) as shown in FIG. 8.

Figure 8:
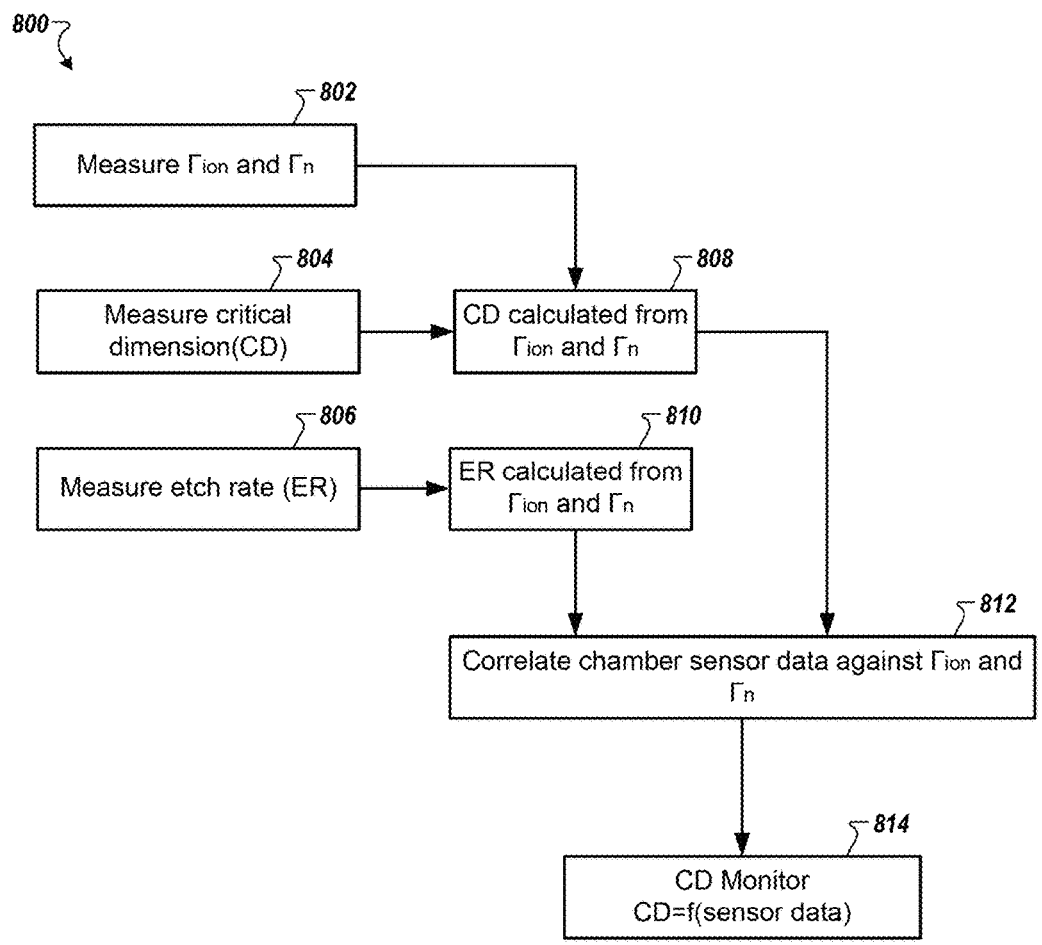
FIG. 8 is a flowchart that shows a matching process according to one example.

FIG. 8 is a flowchart that shows a matching process 800 according to one example. At step 802, the ion flux ($\Gamma_{ion}$) and the neutral flux ($\Gamma_n$) are determined. At step 804, the critical dimension (CD) is measured. At step 806, the etch rate (ER) is measured. At step 808, the critical dimension (CD) is calculated from the ion flux ($\Gamma_{ion}$) and the neutral flux ($\Gamma_n$). At step 810, the etch rate (ER) is calculated from $\Gamma_{ion}$ and $\Gamma_n$. At step 812, the chamber sensor data (i.e., plasma parameters) are correlated against the ion flux ($\Gamma_{ion}$) and the neutral flux ($\Gamma_n$). The ion flux ($\Gamma_{ion}$) is correlated to the peak to peak voltage (Vpp). The neutral flux ($\Gamma_n$) may be correlated to the optical emission spectroscopy (OES) sensor data. At step 814, a critical dimension (CD) monitor as a function of the sensor data may be stored in memory 114.

Although the flow charts show specific orders of executing functional logic blocks, the order of executing the block blocks may be changed relative to the order shown, as will be understood by one of ordinary skill in the art. Also, two or more blocks shown in succession may be executed concurrently or with partial concurrence.

In one implementation, the methodologies described herein may be used to monitor the processing chamber 102. Table 2 shows the status of the processing chamber 102 based on outputs from the methodologies described herein (critical dimension (CD) monitor) and from known fault detection techniques.

TABLE 2

Processing chamber status

| CD monitor | Fault detection | Status |
|---|---|---|
| Within the spec | Within the spec | Run |
| Within the spec | Out of the spec | Warning |
| Out of the spec | — | Abort |

Figure 9:
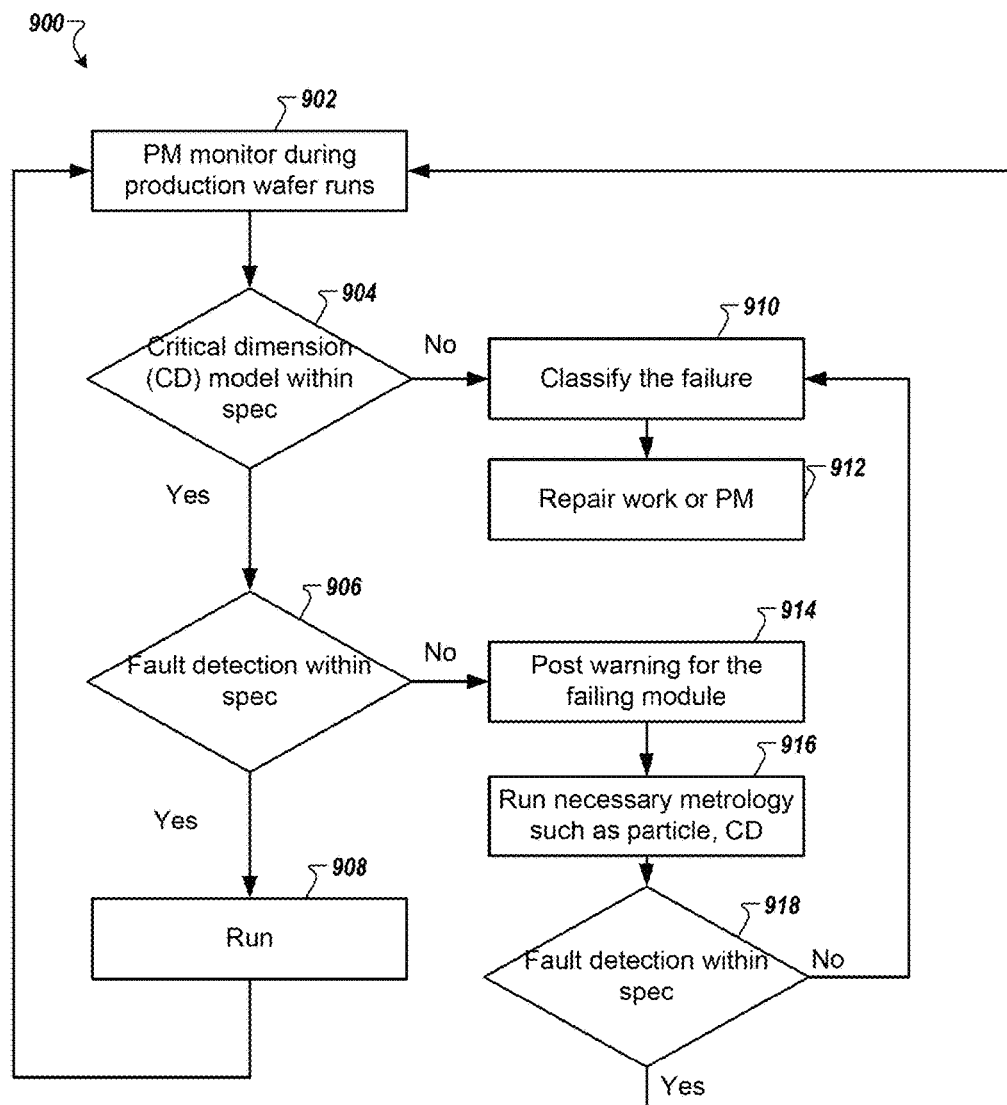
FIG. 9 is a flowchart for a monitoring process according to one example.

FIG. 9 is a flowchart for a monitoring process 900 according to one example. At step 902, a preventive monitor may be enabled for the processing chamber 102. At step 904, the processor 112 may check to see whether one or more variables determined using the methodologies described herein are within the specification. In response to determining that the one or more variables are within the specification, the process proceeds to step 906. In response to determining that the one or more variables are not within the specification, the process proceeds to step 910.

At step 906, the processor 112 may check to see whether one or more variables determined using fault detection (e.g., using a fault detection system) are within the specification associated with the processing chamber 102. In response to determining that the one or more variables are within the specification, the process proceeds to step 908. In response to determining that the one or more variables associated with fault detection are outside the specification, the process proceeds to step 914.

At step 908, the status of the processing chamber 102 may be set to "Run" and the process goes back to step 902 to continue monitoring the processing chamber 102.

At step 910, the status of the processing chamber 102 may be set to "Abort". The processor may classify the failure by using a look-up library. For example, the processor 112 may check for end of life for consumables, drift in microwave/radio frequency (MW/RF) power, and the like. At step 912, repair work or preventive maintenance may be completed.

At step 914, the status may be set to "Warning." For example, the processor 112 may output a warning notification. At step 916, metrology techniques such as particle, critical dimension (CD) may be run. Then at step 918, the processor 112 may check to see whether to see whether one or more metrology results are within the specification. In response to determining that the one or more variables are within the specification the process proceeds to step 902. In response to determining that the one or more variables are not within the specification, the process proceeds to step 910.

In one implementation, multiple warning levels may be implemented. For example, a difference between the one or more variables and the standard one or more variables may be determined. A level one warning may be output if the difference is within a first predetermined threshold (e.g., 10%). A level two warning may be output if the difference exceeds a second predetermined threshold (e.g., 15%). The multiple warning levels provide the operator with information for easy decision whether to continue or stop the process, which function may also be performed by processor 112.

The methods described herein for chamber matching avoid the following drawbacks of prior art chamber matching methods: Using module level diagnostics such as RF probes which are indirectly related to plasma parameters and are also susceptible to sensor to sensor variations; and Using statistical models to define normal and abnormal states of the plasma processing chamber which are again subject to variabilities.

The methods described herein estimates the etch rate (ER) and the critical dimension (CD) based on data obtained from two or three sensors. In addition, based on the data the processor may determine whether the processing chamber is within the specification. Conventional methods measure a high number of parameters (i.e., 10, 15 or more) to determine whether the processing chamber is within the specification, which is unnecessary complicates the models. Here, an understanding of the physical (phenomenological) model relating the etch rate (ER) and the critical dimension (CD) to the ion and neutral fluxes allows for a reduction of the number of monitored plasma parameters to only those that most directly correlate with the ion and neutral fluxes, without any loss of predictive accuracy, but with dramatically increased efficiency due to a reduced number of monitored parameters.

Figure 10:
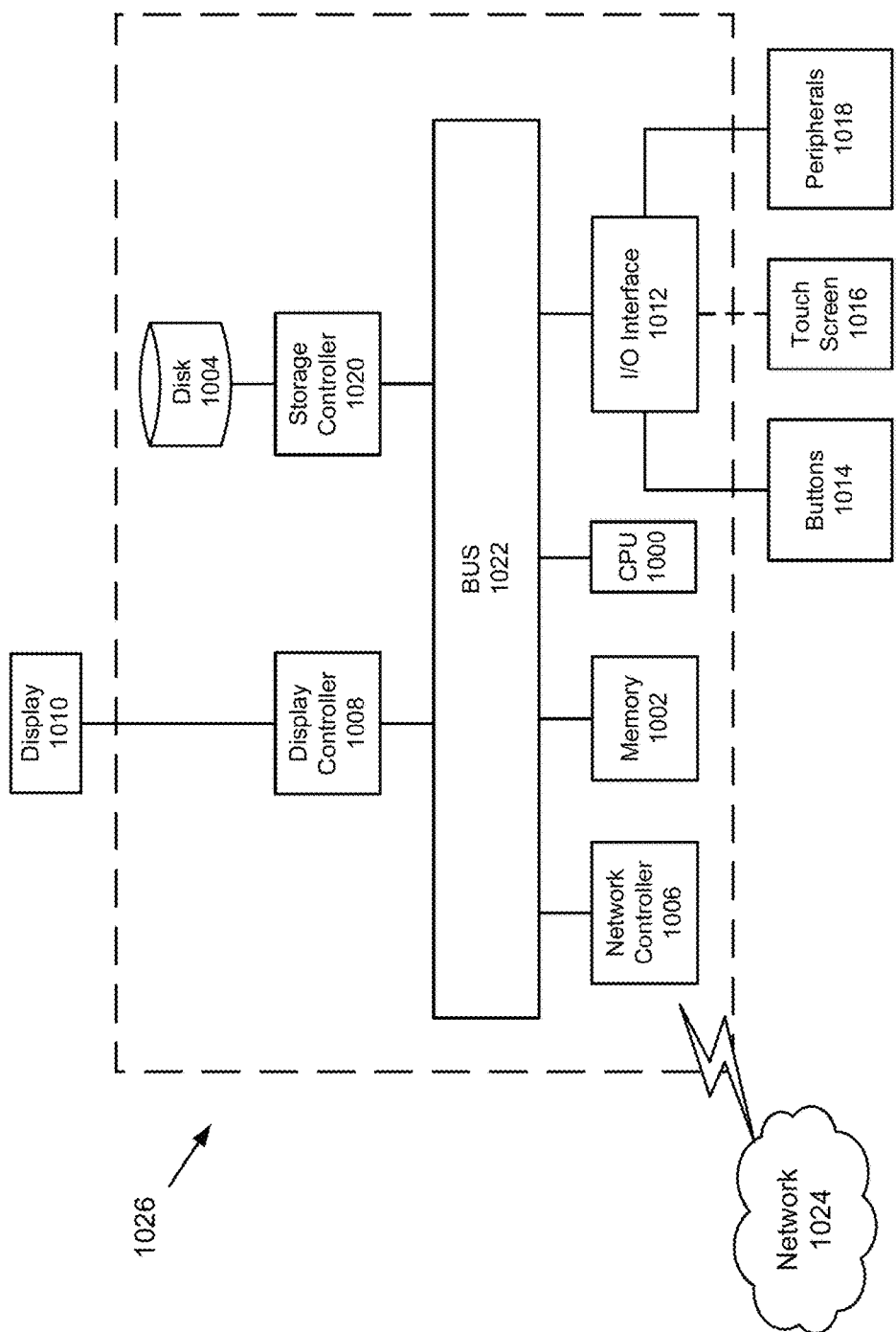
FIG. 10 is a block diagram of a computer according to one example.

In one implementation, the functions and processes of the controller 110 may be implemented by a computer 1026. Next, a hardware description of the computer 1026 according to exemplary embodiments is described with reference to FIG. 10. In FIG. 10, the computer 1026 includes a CPU 1000 which performs the processes described herein. The process data and instructions may be stored in memory 1002. These processes and instructions may also be stored on a storage medium disk 1004 such as a hard drive (HOD) or portable storage medium or may be stored remotely. Further, the claimed advancements are not limited by the form of the computer-readable media on which the instructions of the inventive process are stored. For example, the instructions may be stored on CDs, DVDs, in FLASH memory, RAM, ROM, PROM, EPROM, EEPROM, hard disk or any other information processing device with which the computer 1026 communicates, such as a server or computer.

Further, the claimed advancements may be provided as, a utility application, background daemon, or component of an operating system, or combination thereof, executing in conjunction with CPU 1000 and an operating system such as Microsoft® Windows®, UNIX®, Oracle® Solaris, LINUX®, Apple macOS® and other systems known to those skilled in the art.

In order to achieve the computer 1026, the hardware elements may be realized by various circuitry elements, known to those skilled in the art. For example, CPU 1000 may be a Xenon® or Core® processor from Intel Corporation of America or an Opteron® processor from AMD of America, or may be other processor types that would be recognized by one of ordinary skill in the art. Alternatively, the CPU 1000 may be implemented on an FPGA, ASIC, PLD or using discrete logic circuits, as one of ordinary skill in the art would recognize. Further, CPU 1000 may be implemented as multiple processors cooperatively working in parallel to perform the instructions of the inventive processes described above.

The computer 1026 in FIG. 10 also includes a network controller 1006, such as an Intel Ethernet PRO network interface card from Intel Corporation of America, for interfacing with network 1024. As can be appreciated, the network 1024 can be a public network, such as the Internet, or a private network such as LAN or WAN network, or any combination thereof and can also include PSTN or ISDN sub-networks. The network 1024 can also be wired, such as an Ethernet network, or can be wireless such as a cellular network including EDGE, 3G and 4G wireless cellular systems. The wireless network can also be WiFi®, Bluetooth®, or any other wireless form of communication that is known.

The computer 1026 further includes a display controller 1008, such as a NVIDIA® GeForce® GTX or Quadro® graphics adaptor from NVIDIA Corporation of America for interfacing with display 1010, such as a Hewlett Packard® HPL2445w LCD monitor. A general purpose I/O interface 1012 interfaces with a keyboard and/or mouse 1014 as well as an optional touch screen panel 1016 on or separate from display 1010. General purpose I/O interface also connects to a variety of peripherals 918 including printers and scanners, such as an OfficeJet® or DeskJet® from Hewlett Packard®.

The general purpose storage controller 1020 connects the storage medium disk 1004 with communication bus 1022, which may be an ISA, EISA, VESA, PCI, or similar, for interconnecting all of the components of the computer 1026. A description of the general features and functionality of the display 1010, keyboard and/or mouse 1014, as well as the display controller 1008, storage controller 1020, network controller 1006, and general purpose I/O interface 1012 is omitted herein for brevity as these features are known.

Obviously, numerous modifications and variations are possible in light of the above teachings. It is therefore to be understood that within the scope of the appended claims, the invention may be practiced otherwise than as specifically described herein.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for plasma etching in a plasma etch processing chamber, comprising:
   a) measuring a first set of plasma etch processing parameters including an ion flux ($\Gamma_{ion}$) and a neutral flux ($\Gamma_n$);
   b) determining an etch rate from the measured first set of plasma etch processing parameters;
   c) altering plasma etch processing chamber hardware configuration associated with one or more out-of-specification conditions if the determined etch rate differs from a standard etch rate corresponding to the standard set of etch processing parameters by more than a predetermined etch rate difference threshold, thereafter repeating steps a) through c) until the determined etch rate differs from the standard etch rate by less than the predetermined etch rate difference threshold;
   d) measuring a critical dimension of an etched feature formed on a substrate; and
   e) altering the etch processing parameters for the plasma etch processing if the measured critical dimension differs from a standard critical dimension corresponding to the standard set of etch processing parameters by more than a predetermined critical dimension difference threshold, thereafter repeating steps d) through e) until the measured critical dimension differs from the standard critical dimension by less than the predetermined critical dimension difference threshold.

2. The method of claim 1, wherein measuring the critical dimension of an etched feature comprises measuring the critical dimension using a nondestructive optical measurement method.

3. The method of claim 2, wherein the nondestructive optical measurement method comprises an optical critical dimension (OCD) measurement method.

4. The method of claim 1, wherein measuring the critical dimension comprises indirect measuring of critical dimension from a set of acquired plasma processing parameters using a CD monitor.

5. The method of claim 1, wherein the ion flux ($\Gamma_{ion}$) is measured indirectly from a measured rate of change of temperature of a surface exposed to the plasma in the plasma etch processing chamber.

6. The method of claim 5, wherein the surface exposed to the plasma comprises a surface of a substrate for temperature measurement.

7. The method of claim 1, wherein the neutral flux ($\Gamma_n$) is determined from optical emission spectra (OES) from the plasma.

8. The method of claim 1, wherein the ion flux ($\Gamma_{ion}$) is determined from a peak to peak voltage (Vpp) on a substrate.

9. The method of claim 1, wherein the step of altering etch processing parameters further comprises comparing ion flux ($\Gamma_{ion}$) to a standard ion flux ($\Gamma_{ion\ std}$) corresponding to the standard set of etch processing parameters and comparing neutral flux ($\Gamma_n$) to a standard neutral flux ($\Gamma_{n\ std}$) corresponding to the standard set of etch processing parameters, and altering the etch processing parameters if either flux differs from the standard flux by more than a predetermined difference threshold.

10. A method, comprising:
    monitoring in-situ changes for at least one plasma parameter of a plasma in a vacuum process chamber and at least one process condition in the vacuum process chamber; the process condition being a temperature, a gas flow, a power level, or a power frequency level, the plasma parameter being a density of a constituent of the plasma,
    determining magnitudes of the in-situ changes for the plasma parameter(s) and the process condition(s);
    determining the magnitude changes relative to each other for at least two of the plasma parameter(s), process condition(s), or a combination thereof; and
    adjusting at least one of the process conditions of the vacuum process chamber based, at least in part, at least one magnitude comparison between the plasma parameter(s), the process condition(s), or a combination thereof.

11. The method of claim 10, wherein the adjusting comprises:
    adjusting at least one process condition to achieve a desired result on a substrate.

12. The method of claim 11, wherein the desired result comprises an etch rate value, a critical dimension value, or a combination thereof.

13. The method of claim 10, wherein the one of the in-situ changes comprises a density of a chemical constituent of the plasma.

14. The method of claim 10, wherein the two or more of the plasma parameters, the process conditions, or a combination thereof comprise:
    a voltage of an electrical signal applied to an electrode of the vacuum process chamber; and
    a temperature rate change of a substrate or a substrate holder disposed in the vacuum process chamber.

15. The method of claim 10, wherein the adjusting comprises:
    determining a magnitude of a first one of the in-situ changes being below a first in-situ threshold value based, at least in part, on two or more of the plasma parameters, the process conditions, or a combination thereof;
    adjusting a first process condition to achieve a desired result on a substrate;
    determining a magnitude of a second in-situ change being less than a second in-situ threshold value; and
    adjusting a second process condition to achieve the desired result on a substrate.

16. The method of claim 15, wherein the adjusting the first process condition comprises adjusting a gas flow rate to the vacuum process chamber.

17. The method of claim 15, wherein the adjusting the second process condition comprises adjusting a radio frequency (RF) power applied to an electrode disposed in the vacuum process chamber.

18. The method of claim 15, wherein the adjusting the second process condition comprises adjusting a microwave power applied to a second electrode disposed in the vacuum process chamber.

* * * * *

UNITED STATES PATENT AND TRADEMARK OFFICE
CERTIFICATE OF CORRECTION

PATENT NO. : 10,438,805 B2
APPLICATION NO. : 15/832257
DATED : October 8, 2019
INVENTOR(S) : Jun Shinagawa It is certified that error appears in the above-identified patent and that said Letters Patent is hereby corrected as shown below:

On the Title Page

On Page 2, Column 2, item (56), other publications, Line 6, delete "lo" and insert -- low --, therefor.

In the Specification

In Column 1, Line 47, delete "between," and insert -- between --, therefor.

In Column 2, Line 17, delete "deters fining" and insert -- determining --, therefor.

In Column 2, Line 36, delete "the a" and insert -- the --, therefor.

In Column 2, Line 48, delete "plasma," and insert -- plasma --, therefor.

In Column 3, Line 17, delete "drawings" and insert -- drawings, --, therefor.

In Column 4, Line 42, delete "($\Gamma_r$)" and insert -- ($\Gamma_n$) --, therefor.

In Column 5, Line 44, delete "gas," and insert -- gas --, therefor.

In Column 7, Line 51, delete "406" and insert -- 406, --, therefor.

In Column 8, Line 66, delete "$\Delta F_{ion2}$" and insert -- $\Delta \Gamma_{ion2}$ --, therefor.

In Column 9, Line 38, delete "$\Delta Cl_{2}\text{-}n_{neutral}/1.1$" and insert -- $\Delta Cl_{2}\text{-} \Delta n_{neutral}/1.1$ --, therefor.

In Column 9, Line 51, delete "$\Delta \Gamma_{ion}2 \sim \Gamma_{ion2} -0.3 \times \Delta Cl_2$" and insert -- $\Delta F_{ion}2 \sim \Gamma_{ion2} -0.3 \times \Delta Cl_2.$ --, therefor.

In Column 11, Line 20, delete "specification" and insert -- specification, --, therefor.

Signed and Sealed this
Second Day of June, 2020

Andrei Iancu
*Director of the United States Patent and Trademark Office*

In Column 11, Line 67, delete "(HOD)" and insert -- (HDD) --, therefor.

In Column 12, Line 10, delete "as," and insert -- as --, therefor.